(12) United States Patent
Hedmann et al.

(10) Patent No.: US 8,540,886 B2
(45) Date of Patent: Sep. 24, 2013

(54) DIALYSIS CASSETTES AND RELATED SYSTEMS AND METHODS

(75) Inventors: Frank Hedmann, Volkach (DE); Stephan Klatte, Nienburgh (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/464,264

(22) Filed: May 4, 2012

(65) Prior Publication Data

US 2012/0220937 A1 Aug. 30, 2012

Related U.S. Application Data

(62) Division of application No. 12/542,971, filed on Aug. 18, 2009, now abandoned.

(30) Foreign Application Priority Data

Aug. 18, 2008 (DE) .......................... 10 2008 038 097

(51) Int. Cl.
*C02F 1/00* (2006.01)
(52) U.S. Cl.
USPC ............................ 210/742; 210/149; 604/113

(58) Field of Classification Search
None
See application file for complete search history.

(56) References Cited

U.S. PATENT DOCUMENTS

| | | | |
|---|---|---|---|
| 5,542,919 A | 8/1996 | Simon et al. | |
| 5,836,908 A | 11/1998 | Beden et al. | |
| 6,743,201 B1 | 6/2004 | Dönig et al. | |
| 2002/0045851 A1* | 4/2002 | Suzuki et al. | 604/28 |
| 2008/0021377 A1 | 1/2008 | Kienman et al. | |

FOREIGN PATENT DOCUMENTS

| | | |
|---|---|---|
| EP | 0482858 | 4/1992 |
| EP | 0687474 | 12/1995 |
| EP | 0778033 | 11/1997 |
| EP | 1195171 | 4/2002 |
| EP | 0956876 | 6/2004 |

* cited by examiner

*Primary Examiner* — Dirk Bass
(74) *Attorney, Agent, or Firm* — Fish & Richardson P.C.

(57) ABSTRACT

A method that includes conveying overheated dialysate through a cassette in a manner to reduce the temperature of the overheated dialysate, and a dialysis system including a control unit configured to cause overheated dialysate to be conveyed through a cassette in a manner to reduce the temperature of the overheated dialysate.

9 Claims, 2 Drawing Sheets

DIALYSIS CASSETTES AND RELATED SYSTEMS AND METHODS

CROSS-REFERENCE TO RELATED APPLICATIONS

This application is a divisional of U.S. patent application Ser. No. 12/542,971, filed Aug. 18, 2009, which claims priority under 35 U.S.C. §119(a) to German Patent Application No. 10 2008 038 097.0, filed Aug. 18, 2008, the entire contents of which are hereby incorporated by reference.

TECHNICAL FIELD

This invention relates to dialysis cassettes and related systems and methods.

BACKGROUND

Cassettes for conveying dialysis liquids, such as dialysate, are known. Some known cassettes include connection elements for the connection of solution bags and lines leading to a patient and to a dialysis machine. The cassettes can have at least one pump chamber with an inflow and an outflow port as well as passages for conducting the supplied and conveyed liquid. The passages can be closed by the application of a compressive force acting on the walls of the passages. A heating device can be used for heating the dialysis liquid in the cassette to a desired temperature.

Such cassettes are used, for example, in the area of peritoneal dialysis. During peritoneal dialysis, the peritoneum is filled and emptied with the help of a dialysis machine called a "cycler." The flow of the dialysis liquid, i.e., dialysate, is controlled by a cassette system. During peritoneal dialysis, the dialysate is heated to the desired temperature in the cassette and is subsequently infused into the peritoneum. If an unexpected stoppage of the cycler occurs and the liquid supply to the patient is interrupted, the dialysate is no longer circulated in the cassette. As a result, the dialysate may be heated above the desired temperature due to the inertia of the heating apparatus. The overheated dialysate typically cannot be used for infusion into the patient when the cycler is restarted. Thus, the dialysate is typically discarded and replaced with new dialysate before the peritoneal dialysis treatment resumes.

SUMMARY

In one aspect of the invention, a cassette is provided for conveying liquids, in particular dialysis liquids. The cassette includes connection elements for the connection of solution bags and lines leading to a patient and/or to a dialysis machine. The cassette further includes at least one pump chamber with an inflow port and an outflow port. In addition, the cassette forms lines or passages for conducting the supplied and conveyed liquids through the cassette. The cassette also includes valves for closing the lines. A heating device is provided for heating the liquid present in the passages to a desired temperature (e.g., a preset desired temperature). A control unit is also provided and is configured to conduct (e.g., circulate) liquid heated above the desired temperature until the desired temperature has been reached again.

Reducing the temperature of the liquid allows the liquid to be used again. Excess heat from the overheated liquid can be transferred to the cassette surrounding it by circulating the overheated liquid within the cassette.

In some implementations, at least one temperature sensor is provided for the measurement of the temperature of the liquid in the cassette. In certain implementations, the temperature sensor is positioned within the cassette. In some implementations, the temperature sensor is located on a dialysis machine and cooperates with the cassette when the cassette is positioned in a cassette compartment of the dialysis machine.

In some implementations, two pump chambers are provided between which the liquid can be displaced until the liquid reaches (e.g., cools to) the desired temperature.

In some implementations, the heating device and a heating region of the cassette act as a continuous-flow heater. In such implementations, the heating device and the heating region of the cassette are configured so that liquid is heated as it flows through the heating region of the cassette.

In another aspect of the invention, a method includes displacing a liquid between the two pump chambers of the cassette until the liquid reaches (e.g., cools to) a desired temperature.

In some implementations, when the desired temperature of the liquid is exceeded, the passage to which the line draining the liquid is connected is closed. At the same time, the heating power of the heating device is reduced. The liquid is pumped through one of the pump chambers from a heating region of the cassette into the other pump chamber.

In the event that a high proportion of cool liquid is already present in the pump chamber into which the overheated liquid is conducted, the resulting mixture of liquid (i.e., the mixture of the overheated liquid and the cool liquid) is conveyed in reverse operation through a heating region of the cassette into the other pump chamber in order to simultaneously cool the heating region of the cassette in this process.

If, in contrast, due to the admixture of the overheated liquid in the pump chamber, a liquid overheated at its mixed temperature should result, the mixed liquid is conveyed in forward operation through the heating region of the cassette into the other pump chamber to distribute the excess heat in the cassette.

An additional aspect of the invention relates to a dialysis machine, such as a peritoneal dialysis machine, having a device for the reception of one of the previously described cassettes as well as a pump unit for actuating the pump chambers of the cassette. The dialysis machine includes a heating device configured to heat liquid flowing through a heating region of the cassette and a control unit configured to conduct (e.g., circulate) liquid heated above a desired temperature until the desired temperature has been reached again.

By using certain dialysis cassettes, systems, and methods described herein, a dialysis liquid that may have been overheated can advantageously be returned to a desired temperature without having to discard the liquid. As a result, the total amount of dialysis liquid used during the treatment can be reduced because it is generally unnecessary to discard the overheated dialysis liquid and replace it with new dialysis liquid. In addition, the amount of time required for the treatment can be reduced since it is generally unnecessary to drain the overheated dialysis liquid and then replace it with new dialysis liquid.

Other aspects, features, and advantages will be apparent from the description and drawings, and from the claims.

DETAILED DESCRIPTION

Figure 1:
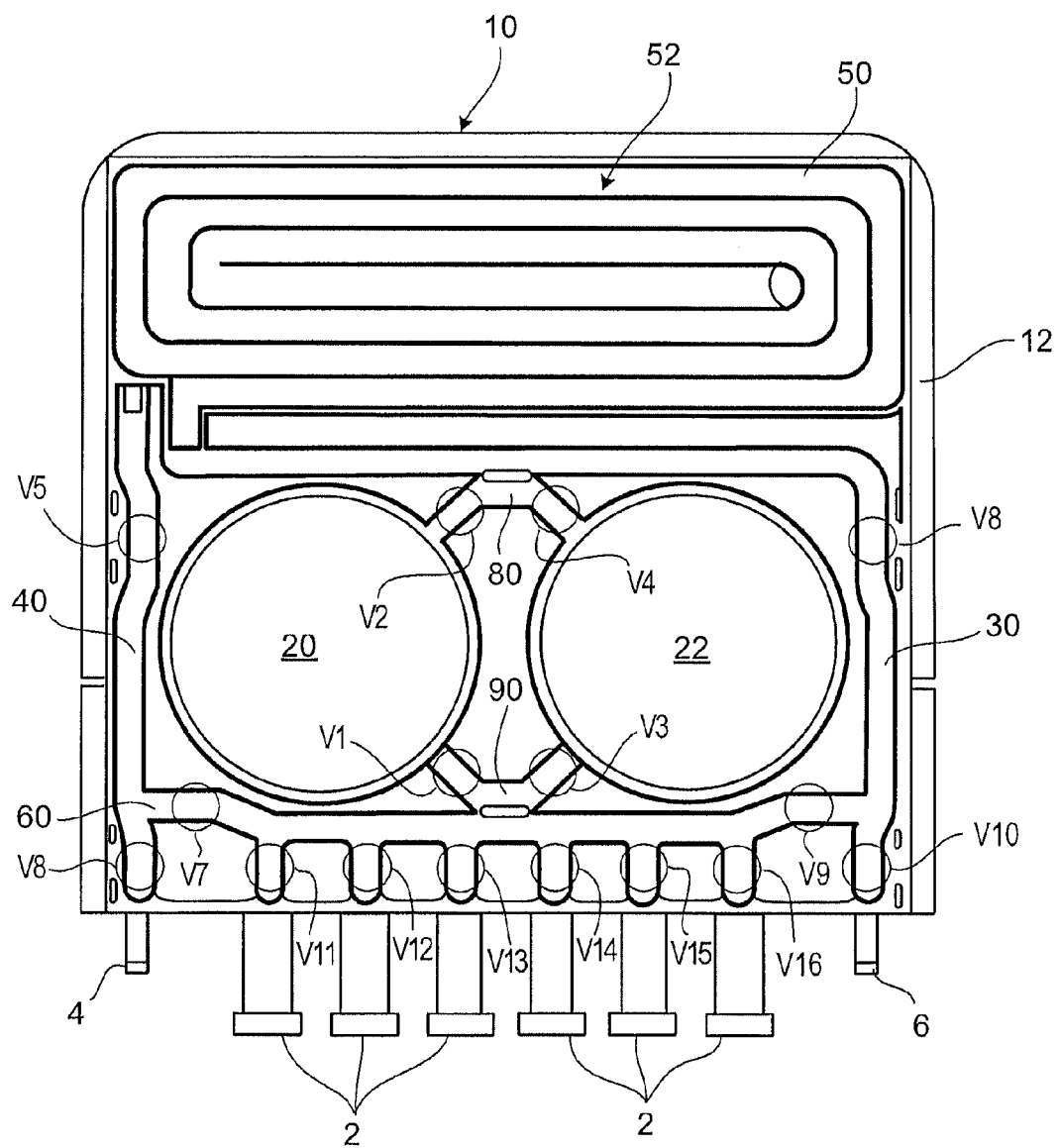
FIG. 1 is a plan view of a dialysis cassette.
Figure 2:
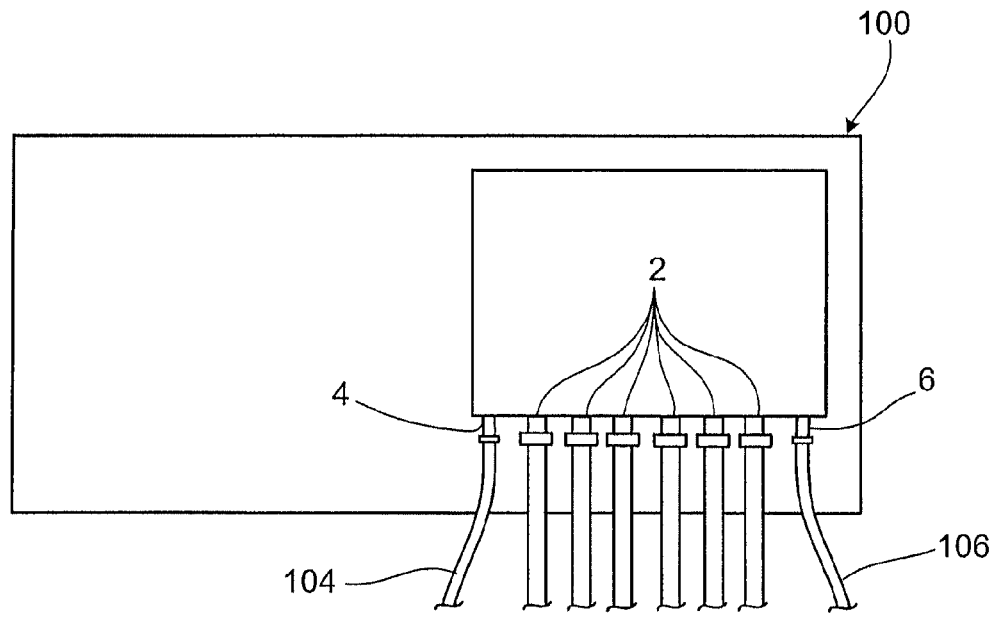
FIG. 2 is a front view of a dialysis system including a dialysis machine and the dialysis cassette of FIG. 1.

FIG. 1 shows a disposable cassette 10 that can be retained in a correspondingly designed cassette compartment or mount of a dialysis machine (e.g., a peritoneal dialysis machine) 100 (shown in FIG. 2). Referring to FIGS. 1 and 2, the reference numerals 2, 4, 6 characterize connection elements for the connection of solution bags, of lines leading to the patient and to the dialysis machine, and of drainage lines. Two fixedly attached hoses or lines 104 and 106 are arranged at the connectors 4 and 6, with one of the hoses representing the patient hose and the other representing the drainage hose. The connection elements 2 allow the operator to connect the solution bags or other medication containers to the cassette 10.

Referring again to FIG. 1, the cassette 10 includes a base body 12 that is made of plastic and can be manufactured using injection molding technology or deep-drawing technology. Cut-outs as well as passages extend in the base body 12. The base body 12 partly forms the walls of two pump chambers 20, 22 arranged next to one another as well as liquid passageways 30, 40, 50, 60 extending within the cassette 10. Liquid passageways 80 and 90 are likewise partly formed by the base body 12 between the pump chambers 20 and 22.

Figure 3:
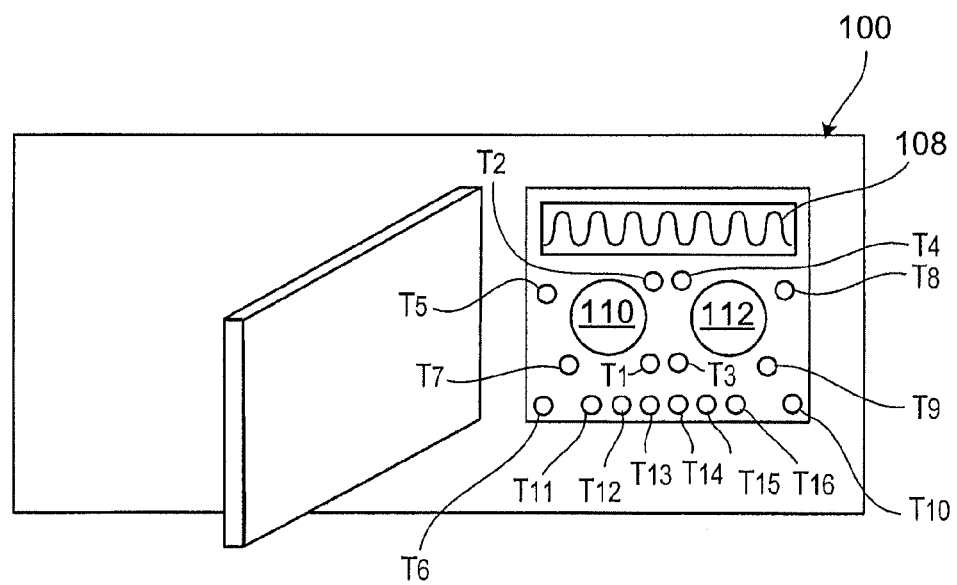
FIG. 3 is a front view of the dialysis machine of FIG. 2 with a door of the dialysis machine open to expose a cassette compartment of the dialysis machine.

The liquid passageway 50 is serpentine shaped and is provided within a heating region 52 of the cassette 10. One end of the passageway 50 is connected to the passageway 30, and the other end of the passageway 50 is connected to the passageway 40. The cassette 10, as discussed above, is configured to be retained in a cassette compartment of the dialysis machine 100. Referring briefly to FIG. 3, the dialysis machine 100 includes a heating device 108. When the cassette 10 is positioned within the cassette compartment of the dialysis machine 100, as shown in FIG. 2, the heating device 108 is positioned adjacent the heating region 52 of the cassette 10 through which the passageway 50 extends. As a result of this arrangement, the dialysis liquid (e.g., dialysate) flowing through the passageway 50 is heated when the cassette 10 is positioned within the cassette compartment of the dialysis machine 100 and the heating device 108 is activated.

As shown in FIG. 3, in addition to the heating device 108, the dialysis machine 100 includes two pumps 110, 112 and multiple valve tappets T1, T2, T3, T4, T5, T6, T7, T8, T9, T10, T11, T12, T13, T14, T15, and T16. The pumps 110, 112 cooperate with the pump chambers 20, 22 to pump liquid through the various passages of the cassette 10. The valve tappets T1, T2, T3, T4, T5, T6, T7, T8, T9, T10, T11, T12, T13, T14, T15, and T16 cooperate with corresponding valves V1, V2, V3, V4, V5, V6, V7, V8, V9, V10, V11, V12, V13, V14, V15 and V16 of the cassette 10 to direct the conveyed liquid through the cassette 10 in a desired manner. The valve tappets T1, T2, T3, T4, T5, T6, T7, T8, T9, T10, T11, T12, T13, T14, T15, and T16 can be pneumatically, hydraulically and/or mechanically controlled.

Other details regarding the cassette and its function substantially correspond to those details and functions described in EP 0 956 876 B1, which is incorporated by reference herein.

During normal function of the cassette 10 and the dialysis machine 100, liquid (e.g., dialysate) is conveyed from the pump chamber 22 through the heating region 52 of the cassette 10 in the direction of the patient line that carries the liquid to the patient and that is connected to the connector 4. The liquid thus flows from the pump chamber 22 via the passageway 80 after the opening of the valve V4 through the passageway 50 adjacent the heater 108 of the dialysis machine 100 and via the opened valve V5 as well as the opened valve V6. As the liquid flows through the passageway 50 adjacent the heater 108, heat emitted from the heater 108 increases the temperature of the liquid. Thus, the heater 108 and the heating region 52 of the cassette 10 together act as a continuous-flow heating mechanism. At the same time that liquid is forced out of the pump chamber 22 and through the passageway 50, the pump chamber 20 is supplied with fresh liquid. The fresh liquid can, for example, be supplied to the pump chamber 20 via the opened valves V11 and V1, while the valves V7, V3 and V2 as well as V9 are simultaneously closed.

If problems arise in the patient line (e.g., if the patient line 104 connected to the connector 4 becomes occluded), the liquid present in the passageway 50 can be overheated due to an overshooting of the heating regulator. The overheated liquid can typically not be infused into the peritoneum due to its elevated temperature.

When overheating of the liquid in the passageway 50 occurs, the valve V6 is closed and the heating power in the heater 108 of the dialysis machine 100 is reduced via a control unit that is arranged in the dialysis machine 100. At the same time, the valve V11 is closed to prevent any additional fresh solution from being delivered to the pump chamber 20. After turning off the heater 108 and closing valves V6 and V11, the overheated solution is pumped via the pump chamber 22 through the passageway 50 adjacent the continuous-flow heater and into the pump chamber 20. To do this, the valve V4, the valve V5, the valve V7, and the valve V1 are opened. The pump stroke of the pump chamber 22 is ended when the pump chamber 20 is filled or the pump chamber 22 is emptied.

Two possibilities now generally result for the cooling of the liquid in dependence on the ratio of the liquid contained in the pump chamber 20 to the warm liquid conveyed into the pump chamber 20.

If a high proportion of cool liquid (i.e., liquid that has not passed through the passageway 50 adjacent the heater 108) is present in the pump chamber 20, the resulting mixed liquid, which is comparatively cooler than the overheated liquid due to the mixing of the liquids, is conveyed via the passageway 50 adjacent the heater 108 into the pump chamber 22 in reverse operation. In particular, the liquid is pumped back into the pump chamber 22 via the opened valve V1, the opened valve V7, the opened valve V5, and the opened valve V4. The partially overheated heating region 52 of the cassette 10 is also cooled by the comparatively cooler liquid.

If, after delivering the overheated liquid to the pump chamber 20, a high proportion of overheated liquid is present in the pump chamber 20, the mixture of liquid (i.e., the mixture of the overheated liquid and any cool liquid that was present in the pump chamber 20 when the overheated liquid was delivered to the pump chamber 20) is conveyed in forward operation via the passageway 50 adjacent the heater 108 into the pump chamber 22. Starting from the pump chamber 20, the liquid is conducted into the pump chamber 22 via the opened valve V2, the opened valve V5, the opened valve V7, and the opened valve V3. In this variant, the excess heat of the overheated liquid is distributed in the cassette so that the temperature of the overheated liquid can be lowered to the desired temperature.

While the heater 108 has been described as being part of the dialysis machine 100 and positioned adjacent to the passageway 50 of the cassette 10 when the cassette 10 is positioned in the cassette compartment of the dialysis machine 100, in certain implementations, the cassette itself includes a heater or part of a heater. The heating region of the cassette can, for example, be equipped with a heating coil. In such cases, the heating coil can be connected to a power supply of the dialysis machine when the cassette is inserted into the cassette compartment in order to provide the coil with power that generates heat.

While the control unit has been described as being part of the dialysis machine 100, the control unit can alternatively be located at any of various other locations outside of the cassette 10.

Other embodiments are within the scope of the claims.

What is claimed is:

1. A method of controlling the temperature of liquid in a dialysis cassette, the method comprising:
   pumping liquid heated to a temperature greater than a desired temperature from a first pump chamber of the dialysis cassette to a second pump chamber of the dialysis cassette, wherein the first pump chamber cooperates with a first pump to pump liquid within the dialysis cassette, and the second pump chamber cooperates with a second pump to pump liquid within the dialysis cassette; and
   pumping the liquid from the second pump chamber of the dialysis cassette back to the first pump chamber of the dialysis cassette, wherein the liquid is pumped back and forth between the first and second pump chambers of the dialysis cassette until the liquid reaches the desired temperature.

2. The method of claim 1, further comprising turning off a heating device configured to heat the liquid in the dialysis cassette, and closing an outlet passage formed in the cassette such that the liquid is substantially prevented from exiting the cassette via the outlet passage.

3. The method of claim 2, wherein a fluid line is connected to the outlet passage and to a patient, and closing the outlet passage substantially prevents the liquid from being delivered via the fluid line to the patient.

4. The method of claim 1, wherein unheated liquid is present in the second pump chamber when the liquid heated to a temperature greater than the desired temperature is pumped into the second pump chamber.

5. The method of claim 4, wherein, when a mixture of the unheated liquid and the liquid heated to a temperature greater than the desired temperature in the second pump chamber is below a given temperature, the mixture is conveyed from the second pump chamber to an outlet passage, then to a heating region of the cassette, then to the first pump chamber.

6. The method of claim 4, wherein, when a mixture of the unheated liquid and the liquid heated to a temperature greater than the desired temperature in the second pump chamber is above a given temperature, the mixture is conveyed from the second pump chamber to a heating region of the cassette, then to an outlet passage, then to the first pump chamber.

7. The method of claim 1, further comprising sensing the temperature of liquid in the cassette.

8. The method of claim 7, wherein the temperature of liquid in a heating region of the cassette is sensed.

9. The method of claim 7, wherein the temperature of liquid in the first pump chamber of the cassette and the temperature of liquid in the second pump chamber of the cassette is sensed.

* * * * *

UNITED STATES PATENT AND TRADEMARK OFFICE
CERTIFICATE OF CORRECTION

PATENT NO. : 8,540,886 B2  Page 1 of 1
APPLICATION NO. : 13/464264
DATED : September 24, 2013
INVENTOR(S) : Frank L. Hedmann and Stephan Klatte It is certified that error appears in the above-identified patent and that said Letters Patent is hereby corrected as shown below:

Title Page, Item (75) (Inventors), delete "Nienburgh" and insert --Nienburg--.

Signed and Sealed this
Sixth Day of May, 2014

Michelle K. Lee
*Deputy Director of the United States Patent and Trademark Office*